US007947285B2

(12) United States Patent
Fein et al.

(10) Patent No.: US 7,947,285 B2
(45) Date of Patent: May 24, 2011

(54) METHODS FOR PREVENTING POST ENDOSCOPIC RETROGRADE CHOLANGIOPANCREATOGRAPHY PANCREATITIS

(76) Inventors: Seymour H. Fein, New Canaan, CT (US); Edward D. Purich, Silver Spring, MD (US); Paul S. Jowell, Chapel Hill, NC (US); John Baillie, Durham, NC (US)

( * ) Notice: Subject to any disclaimer, the term of this patent is extended or adjusted under 35 U.S.C. 154(b) by 208 days.

(21) Appl. No.: 11/130,428

(22) Filed: May 16, 2005

(65) Prior Publication Data

US 2006/0002912 A1 Jan. 5, 2006

Related U.S. Application Data

(63) Continuation of application No. 10/925,400, filed on Aug. 25, 2004, now abandoned.

(60) Provisional application No. 60/529,433, filed on Dec. 12, 2003.

(51) Int. Cl.
*A61K 36/00* (2006.01)
*A61K 36/16* (2006.01)

(52) U.S. Cl. .................. 424/198.1; 514/12.8; 530/350

(58) Field of Classification Search .................. None
See application file for complete search history.

(56) References Cited

U.S. PATENT DOCUMENTS

| 4,443,434 | A | 4/1984 | Lien |
| 4,517,309 | A | 5/1985 | Noda |
| 5,094,837 | A | 3/1992 | Bis |
| 6,020,310 | A | 2/2000 | Beck et al. |
| 6,143,306 | A | 11/2000 | Donovan |
| 6,197,746 | B1 | 3/2001 | Beck et al. |
| 6,261,572 | B1 | 7/2001 | Donovan |
| 6,365,593 | B2 | 4/2002 | Rusche et al. |
| 6,498,143 | B1 | 12/2002 | Beck et al. |
| 6,534,063 | B1 | 3/2003 | Fallon |
| 2001/0018049 | A1 | 8/2001 | Sachs et al. |
| 2003/0133906 | A1 | 7/2003 | Deviere et al. |

OTHER PUBLICATIONS

Devereaux et al. Am J Gastroenterol. 2002; 97: 2279-2281.*
Website at: thefreelibrary.com/_/print/PrintArticle. aspx?id=103446071; 2 pages; downloaded Sep. 9, 2009.*
Website at: docguide.com/dg.nsf/PrintPrint/ B31BAB55A583C66085256D2F006CC24E; 2 pages; downloaded at Sep. 9, 2009.*
Testoni, JOP. J Pancreas (Online) 2004; 5: 171-178.*
Tympner and Röch, Z. Gastroenterologie 1982; 20: 688-693.*
Mundorf et al., American Journal Gastroenterology, 1995; 90: 1611; abstract #229.*
Translation of Tympner and Rösch (see Document V) ; 15 pages total.*
Translation of Tympner and Rosch document: Tympner and Rosch, Z. Gastroenterologie 1982; 20: 688-693; translation document is 15 pages total.*
AGA Council: Abstracts Submitted to the AGA, Gastroenterology, vol. 125, No. 2, pp. 605-607 (Aug. 2003).

* cited by examiner

*Primary Examiner* — Bridget E Bunner
*Assistant Examiner* — Christina Borgeest
(74) *Attorney, Agent, or Firm* — Wiggin and Dana LLP

(57) ABSTRACT

The invention relates generally to methods for preventing post endoscopic retrograde cholangiopancreatography pancreatitis (ERCP). The method comprises administering a therapeutically effective amount of a pharmaceutical composition comprising secretin and a pharmaceutically acceptable carrier.

23 Claims, No Drawings

METHODS FOR PREVENTING POST ENDOSCOPIC RETROGRADE CHOLANGIOPANCREATOGRAPHY PANCREATITIS

CROSS-REFERENCE TO RELATED APPLICATIONS

This application is a Continuation application of U.S. Ser. No. 10/925,400 filed Aug. 25, 2004, now abandoned, which claims the benefit of U.S. Provisional Application Ser. No. 60/529,433 filed Dec. 12, 2003. Both of these applications are incorporated by reference herein in their entireties.

BACKGROUND OF THE INVENTION

1. Field of the Invention

The invention relates generally to methods for preventing post endoscopic retrograde cholangiopancreatography (ERCP) pancreatitis in patients. In this treatment, the method comprises administering a therapeutically effective amount of a pharmaceutical composition comprising secretin and a pharmaceutically acceptable carrier.

2. Brief Description of the Related Art

Endoscopic retrograde cholangiopancreatography (ERCP) is a commonly used diagnostic and therapeutic procedure that involves the injection of contrast and the performance of various therapeutic procedures (e.g., stone extraction, stent replacement, and the like). Over 700,000 such procedures are done annually in the U.S. Gastroenterologists perform this procedure for several reasons, including the evaluation of abdominal pain, the diagnosis of gallstones, the evaluation and diagnosis of diseases of the liver and pancreas, and to remove gallstones.

As with any medical procedure, there are risks associated with ERCP. Risks include punctures to the esophagus, bile duct or pancreatic duct, bleeding, and infection. The most common complication that can occur after ERCP is pancreatitis, commonly known as post-ERCP pancreatitis (Baillie J, Endoscopy 26:185-203, 1994; Sherman S, et al., Pancreas 6:350-367, 1991). Post-ERCP pancreatitis can cause a variety of conditions, including substantial morbidity, rare mortality, and increased costs. Its incidence ranges from 1-12% (mean approximately 7%), depending on the patient and the institution (Bilboa M K et al., Gastroenterology 70:314-320, 1976; Cotton P B, Gut 13:1014-25, 1972; Ruppin H et al., Endoscopy 6:94-8, 1974; Nebel O T et al., Gastrointest Endosc 22:34-6, 1975; LaFerla G et al., Pancreas 1:60-63, 1986; Rozler M H J et al., Radiology 157:595-8, 1985; Hamilton I et al., Clin. Radiol. 34:543-6, 1983; Brandes J W et al., Endoscopy 13:27-30, 1981; Nordback I et al., Ann. Chir. Gynaecol. 77:15-20, 1988). The incidence is higher in patients undergoing cholangiography with pancreatography than for those undergoing cholangiography alone, but is significant in both groups (Sherman et al., (1991); LaFerla G, et al., Pancreas 1:60-63 (1986); Skude G et al., Gut 17:127-32 (1976)). The severity of pancreatitis varies from mild, requiring minimal analgesia and outpatient management, to severe leading to the need for hospitalization, surgery, and in rare instances causing death.

A number of factors may play a role in the pathogenesis of post-ERCP pancreatitis. When associated with pancreatography, the pressure of the contrast injection alone can cause pancreatic injury and repeated injections are associated with a higher incidence of pancreatitis. The contrast agents themselves have been suggested to be potentially injurious; however, trials comparing ionic and non-ionic contrast have not shown a consistent difference in the incidence of post-ERCP pancreatitis.

Direct injection of contrast into the pancreatic duct is not the only factor involved in the genesis of post-ERCP pancreatitis, however, as those undergoing cholangiography alone are also subject to this complication. It is likely that irritation, inflammation or induced spasm of the sphincter of Oddi also plays a significant role. Of note, the incidence of post-ERCP pancreatitis increases with number of attempts at duct cannulation.

It is difficult to estimate the costs associated with the management of post-ERCP pancreatitis. Based on the assumption of a 1% risk of severe pancreatitis, a 3% risk of moderate pancreatitis and a 3% risk of mild pancreatitis, the costs can easily exceed 500 dollars per patient. Combined with lost work and productivity, it is clear that an effective prophylactic regimen to prevent post-ERCP pancreatitis would be of great medical benefit.

Many medical interventions have been tried to prevent post-ERCP pancreatitis, including anticholinergics, antihistamines, corticosteroids, and antibiotics. Drugs that have been evaluated in controlled clinical trials include gabexate, somatostatin, octreotide, nifedipine, hydrocortisone, methylprednisolone, prednisone, interleukin-10, non-ionic contrast agents, glucagon, antibiotics, and calcitonin (Jowell P S et al. Gastroenterology 125(2):605, 2003; Renner I G et al., J. Clin. Invest. 72(3):1081-92, 1983; Niederau C et al., Gastroenterology 88(5 Pt 1): 1192-204, 1985; Renner I G et al., Dig. Dis. Sci. 31(3):305-13, 1986; Keim V et al., Hepatogastroenterology 32(2):91-6, 1985; Infantino A et al., Research in Experimental Medicine 190(2):89-93, 1990; Lankisch P G et al., Digestion 26(4):187-91, 1983; Manso M A et al., Peptides 10(2):255-60, 1989; Tymper F et al., Hepatogastroenterology 33(4):159-62, 1986; Kozarek R A et al., Gastrointest. Endosc. 51:AB138, 2000; Information from MD Consult Drug Information on Secretin. Mosby's Drug Consult (© 2003 Mosby, Inc.); Howard-McNatt M et al., Journal of Surgical Research 103; 96-99, 2002). Three agents—somatostatin, its octapeptide analog octreotide, and gabexate mesylate (a protease inhibitor) showed initial promise. Octreotide reduces hyperamylasemia but has not been show to alter the clinical course of post-ERCP pancreatitis. A meta-analysis of 28 clinical trials showed that both prophylaxis with somatostatin and gabexate were effective in reducing the frequency of post-ERCP pancreatitis. However, in two large controlled trials in which pharmacologic prevention was provided to high-risk patients, gabexate, somatostatin and octreotide were each found to be ineffective in preventing post-ERCP pancreatitis. Additionally, a retrospective review of 4833 ERCP procedures suggested secretin might decrease the incidence of post-ERCP pancreatitis in patients without pancreas divisum (Mundorf J B et al., Am. J. Gastroenterology 90(9):1611, 1995; Mundorf J B et al., Am. J. Gastroenterology 90(9): 1610, 1995). However, none of these approaches has proved consistently effective in clinical trials.

Examples of treatments for post-ERCP pancreatitis in the patent literature include the following:

U.S. Pat. No. 6,143,306 assigned to Allergan Sales, Inc., discloses a non-radio therapy therapeutic method of treating disorders of the pancreas such as pancreatitis using a neurotoxin such as botulinum toxin.

U.S. Pat. No. 6,261,572 assigned to Allergan Sales, Inc., discloses a method for treating a pancreatic disorder by local administration of a therapeutic amount of a neurotoxin such as botulinum toxin, into or onto the body of the pancreas in order to treat symptoms of a pancreatic disorder.

U.S. Published Patent Application No. U.S. 2003/0132906 assigned to Schering-Plough Corporation, discloses the use of interleukin-10 (IL-10) for the prevention and treatment of pancreatitis. This patent discloses that IL-10 is administered to patients at risk of developing pancreatitis due to a procedure such as ERCP.

U.S. Pat. No. 5,094,837 assigned to Wayne State University discloses a method for using magnetic resonance imaging (MRI) to image the pancreas by using secretin. An amount of secretin is placed in solution and administered to a patient for the purpose of pancreatic imaging. Administration of the secretin is done by IV infusion. The secretin employed in this method can be extracted from porcine or bovine sources or can be genetically recombined porcine, bovine or human secretin.

U.S. Pat. No. 6,020,310 and U.S. Pat. No. 6,498,143, both assigned to Repligen, disclose use of secretin to stimulate pancreatico-biliary fluid secretion in a patient exhibiting autism.

U.S. Pat. No. 6,197,746 assigned to Repligen Corporation discloses methods of using secretin for treating autism.

U.S. Pat. No. 6,365,593 assigned to Repligen Corporation discloses methods of diagnosing individuals for autistic disorders, comprising obtaining a sample of urine from the individuals; measuring a level of a methylxanthine in the urine sample; and comparing the level to a normal control or to a threshold level.

U.S. Pat. No. 6,534,063 to Joan Fallon discloses methods of utilizing the fecal chymotrypsin level of an individual as a measure of the success of secretin, other neuropeptides, and peptides or digestive enzyme administration to such individuals, and in particular, as a prognosticative of potential secretin, other neuropeptides, peptides, and digestive enzyme administration for persons having ADD, ADHD, Autism and other PDD related disorders.

There is a need in the art for a prophylactic treatment or medication for post-ERCP pancreatitis. The present invention is believed to be an answer to that need.

SUMMARY OF THE INVENTION

In one aspect, the present invention is directed to a method for preventing post endoscopic retrograde cholangiopancreatography pancreatitis (ERCP), comprising the step of administering to a patient a therapeutically effective amount of a pharmaceutical composition comprising secretin and a pharmaceutically acceptable carrier.

These and other aspects will become apparent upon reading the following detailed description of the invention.

DETAILED DESCRIPTION OF THE INVENTION

It has now been unexpected found that secretin is effective for preventing post endoscopic retrograde cholangiopancreatography pancreatitis (ERCP pancreatitis).

In accordance with one embodiment of the method of the present invention, the treatment for preventing post-ERCP pancreatitis includes administering to a patient in need of such treatment a pharmaceutical composition comprising secretin prior, during, or immediately after ERCP is performed on that patient. It has been unexpectedly discovered that administering an effective amount of secretin during ERCP prevents the occurrence of post-ERCP pancreatitis. An important advantage of this embodiment of the present invention is the avoidance of unwanted side effects, such as pancreatitis, which can be a dangerous, or deadly affliction, during the ERCP procedure.

Secretin is a 3055.5 MW (27 amino acid) gastrointestinal peptide hormone originally extracted from the porcine duodenum. The primary action of secretin is to increase the volume and bicarbonate content of pancreatic juice (Gutierrez L V, et al., Gut 13:721-25 (1972); Laugier R, et al., Digestion 54:54-60 (1993); Cavallini G, et al., Dig. Dis. Sci. 37(1):93-96 (1992)). It also increases the pancreatic duct diameter (Glaser J, et al., Int. J. Pancreatol. 15:195-200 (1994); Tulassay Z, et al., Gastroenterol. J. 51:47-50 (1991)) and causes sphincter of Oddi relaxation (Geenen J E et al., Gastroenterology 78:317-24 (1980); Laugier R. Endoscopy 26:222-27 (1994)). Recently, a new synthetic porcine secretin has been developed that has been shown to be equally effective as a pancreatic secretagogue. In the methods of the invention, secretin may be used from any source. Preferably the secretin used in the methods of the present invention is the naturally occurring form, the synthetic form, or the genetically recombined form of porcine, bovine or human secretin. More preferably the secretin is synthetic porcine secretin. One useful form of secretin is manufactured by ChiRhoClin, Inc. (Burtonsville, Md.) and sold under the trade names SecreFlo™ and SecreMax™ by Repligen Corporation (Waltham, Mass.).

The secretin may be combined with a pharmaceutically acceptable carrier to form a pharmaceutical composition. Thus, the pharmaceutical compositions of this invention comprise secretin from any source (including pharmaceutically acceptable salts thereof) in combination with any pharmaceutically acceptable carrier, adjuvant or vehicle. Pharmaceutically acceptable carriers, adjuvants and vehicles that may be used in the pharmaceutical compositions of the present invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

There are several possible mechanisms by which secretin might prevent post-ERCP pancreatitis. While not wishing to be bound by any particular theory, it is believed that secretin causes release from the pancreatic parenchyma of a large volume of water, bicarbonate, and potentially harmful digestive enzymes, which can cause pancreatic inflammation. In addition, secretin, by increasing exocrine pancreas secretion, may flush the pancreatic ducts after ERCP. Moreover, the increased volume and bicarbonate content of the pancreatic juice stimulated by secretin may dilute and neutralize the possible deleterious effects of contrast media typically injected during ERCP procedures. Secretin may also help prevent acinarization, known to be associated with increased risk of post-ERCP pancreatitis by exerting forward pressure against the pressure of injected contrast media and by increasing ductal diameter allowing the pancreatic duct to accept more contrast. Secretin may also facilitate pancreatic duct cannulation by relaxing the sphincter of Oddi causing the papilla to open, thus reducing the number of attempts needed to cannulate the pancreatic duct.

To produced the pharmaceutical composition of the invention, secretin and a pharmaceutically acceptable carrier are combined, preferably in liquid form, using techniques known in the art. The pharmaceutical compositions of this invention may be administered by any route that produces acceptable bioavailability. Suitable administration methods include, but are not limited to, parenteral methods such as intravenous, subcutaneous and intramuscular and per os (by mouth), or sublingual, and transdermal bolus or continuous infusions of secretin may be used.

The compounds of the invention are preferably administered internally, e.g., intravenously, in the form of conventional pharmaceutical preparations, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical preparations can be in conventional solid forms, for example, tablets, dragées, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation of the invention should include an amount of secretin effective for preventing post-ERCP pancreatitis or preventing acute pancreatitis. The effective dosage will depend on several factors, including body weight, body mass index, age, gender and disease severity. Suitable dosages may be, for example, in the range of about 2 to 50 micrograms secretin, more preferably of about 8 to about 36 micrograms secretin, and most preferably between 15 and 20 micrograms secretin. In addition, multiple doses of secretin may be administered over a period of time (for example, a first dose of 16 micrograms secretin (approximately 0.2 micrograms per kilogram body weight), followed by a second dose of 8 micrograms secretin).

Without being bound by any theory, there are several possible explanations for the protective effect of secretin. Secretin causes release from the pancreatic parenchyma, of a large volume of bicarbonate along with potentially harmful enzymes. Depleting this pool of enzymes may explain why pancreatography after secretin injection is associated with less pancreatitis. By virtue of the increased pancreatic exocrine secretion, secretin may also act to "flush" the duct after ERCP. Furthermore, the increased volume and bicarbonate content of the pancreatic exocrine secretions may dilute and neutralize the possibly deleterious chemical effects of injected contrast. Additionally, secretin may help prevent acinarization, known to be associated with increased risk of post-ERCP pancreatitis, in two ways. First, increased exocrine secretin provides "forward" pressure (resistance) against the pressure of the contrast injection, and, second, the increased ductal diameter associated with secretin administration may increase the pancreatic duct's capacity to accept contrast. Finally, secretin appears to facilitate pancreatic duct cannulation, possibly because increased exocrine pancreas secretions and relaxation of the sphincter of Oddi cause the papilla to "open", thereby decreasing the number of attempts required for successful cannulation. The risk of post-ERCP pancreatitis has been shown to increase with the number of attempts to cannulate the pancreatic duct (Hamilton I, et al., Clin. Radiol. 34:543-6 (1983)).

EXAMPLES

The invention is further described by the following Examples, but is not intended to be limited by the Examples. All parts and percentages are by weight and all temperatures are in degrees Celsius unless explicitly stated otherwise.

A. Study of Intravenous Secretin Administration Prior to Endoscopic Retrograde Cholangiopancreatography (ERCP) for the Prevention of Post-ERCP Pancreatitis 1. Objectives The objectives of this study were to assess the efficacy of synthetic porcine secretin (sPS) in preventing post-ERCP pancreatitis, assess the cost effectiveness of using sPS for prevention of post-ERCP pancreatitis; and to assess the safety of sPS.

2. Investigational Plan and Selection of Study Population

This was a prospectively randomized, parallel group, double-blind, placebo controlled study conducted at one center. This was the ideal study design for evaluation of the prophylactic use of sPS in ERCP to decrease the incidence of post-ERCP pancreatitis. Parallel group design was necessary because patients usually require only one ERCP and, in any case, the first procedure might have an unknown effect on the outcome of a subsequent ERCP. Double-blinding the study was necessary because a major component of the evaluation related to symptoms such as pain and nauseas, which are, in part, subjective for the patient. The final classification of each patient required an overall medical judgment by the investigator. In order for this to be as objective as possible, the assessor (Principal Investigator) had to be blinded. Placebo control with normal saline was required because there is no approved or medically accepted drug to prevent post-ERCP pancreatitis. Further, sterile normal saline, USP for injection was completely safe with no pharmacological effect and produced a clear, colorless solution, which was indistinguishable from reconstituted sPS.

Patients undergoing ERCP for medical reasons were the appropriate population to evaluate because only those requiring ERCP have the procedure and are subject to the known risk of post-ERCP pancreatitis. The patients had to meet all of the inclusion criteria to be enrolled in the study. Those criteria included (1) patient is undergoing ERCP for medical reasons; (2) age ≧18 years (no upper limit); (3) able and willing to sign informed consent according to Institutional Review Board guidelines; (4) patient's physician agreed to their involvement in the trial. In addition, the patient was required to not exhibit any of the exclusion criteria to be enrolled in the study. Exclusion criteria included (1) ongoing, active acute pancreatitis at the time of the procedure (patients with chronic pancreatitis were not excluded); (2) known adverse reaction to secretin; (3) recent (within one month) use of medication that is known to cause pancreatitis; (4) pregnant woman, nursing mothers, or women of child bearing potential not employing appropriate contraception or abstinence; (5) known or newly diagnosed pancreas divisum at the time of the ERCP; and (6) patients undergoing biliary or pancreatic manometry. Subjects were discontinued for the following reasons: (1) voluntary withdraw at subject's request; (2) noncompliance by subject to study procedures; (3) protocol violation such as discovery of pancreas divisum at the time of the ERCP, or (4) excessive toxicity from any study procedure or drug which in the judgment of the investigator makes continuation in the study contrary to the subject's medical interests. Subjects who discontinued from the study after receiving study drug were followed for safety and were replaced.

3. Treatments

This study compared synthetic porcine secretin (sPS) at a dose of 16 mcg (8 mL) (24 mcg for procedures longer than 30 minutes) given as a slow IV push over one minute and an equal volume of physiologic sterile saline USP for injection. Subjects were randomly assigned to one of two treatment groups (sPS vs. saline placebo) based on a randomization schedule generated at ChiRhoClin, Inc (Burtonsville, Md.). Directions for preparation of sPS or saline were provided to a research nurse who was not involved in the procedure and who prepared the study drug in a separate area from the ERCP suite, to which study personnel did not have access. The final syringe with an identical appearing clear, colorless solution of identical volume containing either reconstituted sPS or saline was then delivered to the investigator performing the ERCP. The randomization code assigned patients in a 1:1 manner between the two treatments and was balanced in blocks of 250 patients.

The dose of 16 mcg of sPS was an approximation of the standard dose of 0.2 mcg (1 CU) per kg used in the secretin stimulated pancreatic function test in which IV dose response studies including CRC97-1 was shown to produce near maximal stimulation of the exocrine pancreas. Patients were not allowed to have received any medication known to cause pancreatitis within one month of enrollment in the study. Antiemetics such as Compazine and Phenergan were allowed for nausea and vomiting. Fluid replacement was used to treat hypotension. Other medications required by patients during and after ERCP procedure were allowed.

4. Efficacy and Safety Variables

Incidence of post-ERCP pancreatitis (sPS vs. placebo) was evaluated as the primary efficacy variable in this study. Secondary efficacy variables included incidences of post-ERCP pancreatitis in the following sub-populations: (1) cannulation of CBD; (2) sphincterotomy of CBD; (3) cannulation of pancreatic duct; (4) sphincterotomy of pancreatic duct; (5) stent insertion and removal into CBD; (6) stent insertion and removal into pancreatic duct; (7) stone extraction (basket) from CBD; (8) stone extraction (balloon) from CBD; (9) manometry of CBD; (10) manometry of pancreatic duct; (11) pain scores pre and post ERCP (0-10 scale); (12) nausea scores pre and post ERCP (0-10 scale); (13) vomiting scores pre and post ERCP (0-10 scale); (14) return to baseline activity (pre-ERCP); and (15) return to work.

In addition, the severity of pancreatitis was graded as defined by Cotton (Cotton, PB Gastrointest. Endosc. 40(4): 514-18 (1994)), using the following criteria: (1) Minimal—managed on an outpatient basis; (2) Mild—Required hospitalization ≦3 days; (3) Moderate—required hospitalization for 4 to 10 days; and (4) Severe—required hospitalization for >10 days, ICU admission, surgical intervention or death.

This study evaluated the following safety variables: (1) Adverse events; (2) Vital signs; (3) Serum Amylase (when clinically indicated); and (4) Serum Lipase (when clinically indicated). No drug concentration measurements were assessed in this study.

5. Statistical and Analytical Methods

The demographic variables of age, gender, race, weight and height were compared between the treatment groups using the Fisher Exact Test. Medical history variables of tobacco use and alcohol use were compared between treatment groups using Fisher Exact Test.

Primary and secondary efficacy variables were compared between the treatment groups using the Fisher Exact Test or Cochran-Mantel Haenszel Association Test. Adverse events and vital signs (heart rate, blood pressure) were compared between the treatment groups using the t-test. The clinical assumption on which the power calculation is based was on incidence of post-ERCP pancreatitis among all patients without pancreas divisum of 6%. In order to show a 50% reduction in the rate of post-ERCP pancreatitis with a significance of $p=0.05$, at a power of 80%, 749 evaluable patients per treatment group (sPS vs. placebo) were needed.

6. Efficacy Evaluation

A total of 979 patients were randomized, received study drug and were evaluable for efficacy. The demographic profiles of the patients who were randomized and received treatment with study drug by treatment group are summarized in Table 1.

TABLE 1

Demographic Characteristics

| Parameter | Treatment Group | | p-value |
|---|---|---|---|
| | SPS | Placebo | |
| Age (years) | N = 488 | N = 491 | |
| Mean (SD) | 55.6 (16.3) | 55.8 (17.0) | 0.8650 |
| Range (min-max) | 17.0-93.0 | 18.0-91.0 | |
| Weight (kg) | N = 488 | N = 491 | |
| Mean (SD) | 76.4 (20.5) | 76.8 (23.2) | 0.7734 |
| Range (min-max) | 36.0-208.0 | 36.0-241.0 | |
| Height (cm) | N = 488 | N = 491 | |
| Mean (SD) | 167.9 (15.0) | 168.3 (13.2) | 0.6356 |
| Range (min-max) | 59.0-198.0 | 16.0-200.0 | |
| Gender (%) | N = 488 | N = 491 | |
| Male (%) | 225 (46.11) | 203 (41.34) | 0.1387 |
| Female (%) | 263 (53.29) | 288 (58.66) | |
| Race (%) | N = 486 | N = 490 | |
| Caucasian | 396 (81.48) | 395 (80.61) | 0.7986 |
| African-American | 81 (16.67) | 88 (17.96) | |
| Hispanic | 2 (0.41) | 1 (0.20) | |
| American Indian | 4 (0.82) | 5 (1.02) | |
| Asian | 3 (0.62) | 1 (0.20) | |
| Tobacco Use (%) | N = 482 | N = 487 | |
| Yes | 154 (31.98) | 127 (26.08) | 0.0475 |
| No | 328 (68.05) | 360 (73.92) | |
| Alcohol Use (%) | N = 481 | N = 483 | |
| Yes | 112 (23.28) | 119 (24.64) | 0.6510 |
| No | 369 (76.72) | 364 (75.36) | |
| History of Post-ERCP Pancreatitis | N = 442 | N = 490 | |
| Yes (%) | 26 (5.88) | 22 (5.00) | 0.6566 |
| No (%) | 416 (94.12) | 418 (95.00) | |

Statistical Method = Chi-Square

The two treatment groups were similar in all demographic characteristics. The only marginally significant difference was in the frequency of tobacco use by medical history, which was more common in the group treated with sPS ($p=0.0475$). There were slightly more males and fewer females in the sPS group, but this was not a statistically significant difference. Overall, the two treatment groups were well matched demographically.

During an ERCP, a variety of diagnostic and therapeutic procedures may be performed by the endoscopist depending on the medical purposes of the ERCP, the medical condition of the patient and the observations made during the ERCP. A comparison of the frequency of these procedures between the two treatment groups appears in Table 2.

TABLE 2

Incidence of Intra-ERCP Procedures

| Procedure | Treatment Group | | p-value |
|---|---|---|---|
| | SPS (N = 488) | Placebo (N = 491) | |
| Cannulation CBD (%) | | | |
| Yes | 361 (73.98) | 368 (74.95) | 0.7695 |
| No | 127 (26.02) | 123 (25.08) | |

TABLE 2-continued

Incidence of Intra-ERCP Procedures

| Procedure | Treatment Group | | p-value |
|---|---|---|---|
| | SPS (N = 488) | Placebo (N = 491) | |
| Cannulation of Pancreatic Duct (%) | | | |
| Yes | 220 (45.08) | 219 (44.60) | 0.8978 |
| No | 268 (54.92) | 272 (55.40) | |
| Sphincterotomy of CBD (%) | | | |
| Yes | 140 (28.69) | 159 (32.38) | 0.2125 |
| No | 348 (71.31) | 332 (67.62) | |
| Sphincterotomy of Pancreatic Duct (%) | | | |
| Yes | 26 (5.34) | 30 (6.11) | 0.6802 |
| No | 461 (94.66) | 461 (93.89) | |
| Stent Removal from CBD (%) | | | |
| Yes | 58 (11.93) | 59 (12.02) | 1.0000 |
| No | 428 (88.07) | 432 (87.98) | |
| Stent Removal from Pancreatic Duct (%) | | | |
| Yes | 17 (3.56) | 17 (3.46) | 1.0000 |
| No | 469 (96.50) | 474 (96.54) | |
| Stent Insertion into CBD (%) | | | |
| Yes | 108 (22.22) | 116 (23.67) | 0.6480 |
| No | 378 (77.78) | 375 (76.37) | |
| Stent Insertion into Pancreatic Duct (%) | | | |
| Yes | 23 (4.73) | 42 (8.55) | 0.0203* |
| No | 463 (95.27) | 449 (91.45) | |
| Stone Extraction (Basket) from CBD (%) | | | |
| Yes | 35 (7.20) | 48 (9.78) | 0.1687 |
| No | 451 (92.80) | 443 (90.22) | |
| Stone Extraction (Balloon) from CBD (%) | | | |
| Yes | 55 (11.32) | 70 (14.26) | 0.1806 |
| No | 431 (88.68) | 421 (85.74) | |
| Manometry of CBD (%) | | | |
| Yes | 19 (3.91) | 17 (3.46) | 0.7370 |
| No | 467 (96.09) | 474 (96.54) | |
| Manometry of Pancreatic Duct (%) | | | |
| Yes | 11 (2.26) | 7 (1.43) | 0.3526 |
| No | 475 (97.74) | 484 (98.57) | |

*Chi-Square Test

The two groups were well matched with regard to the types and incidences of various intra-ERCP procedures performed. The only statistically significant difference was in the frequency of stent insertion into the pancreatic duct (42 cases in the placebo group vs. 23 cases in the sPS group). As described in more detail below, the incidence of post-ERCP pancreatitis in the sPS group was actually slightly higher (5/23=21.7%) than in the placebo group (8/42=19%). Only 3 additional cases of post-ERCP pancreatitis occurred in the placebo group vs. the sPS group in this patient population.

The primary efficacy variable was the overall incidence of post-ERCP pancreatitis. The results are depicted in Table 3.

TABLE 3

Overall Incidence of Post-ERCP Pancreatitis

| Parameter | Treatment Group | | p-value |
|---|---|---|---|
| | SPS (N = 488) | Placebo (N = 491) | |
| Incidence of Post-ERCP Pancreatitis | | | |
| Yes (%) | 44 (9.02) | 69 (14.05) | 0.0161* |
| No (%) | 444 (90.98) | 422 (85.95) | |

*Fisher Exact Test

The difference in the incidence of post-ERCP pancreatitis between the two treatment groups in favor of the sPS treated patients was highly significant. The p-value of 0.0161 was sufficient to allow the study to be discontinued on the basis of the planned interim analysis of approximately 1,000 evaluable patients. The severity of the cases of post-ERCP pancreatitis, which did occur in each treatment group is depicted in Table 4 below.

TABLE 4

Post-ERCP Pancreatitis Severity

| Severity Rating (%) | Treatment Group | | p-value | Overall |
|---|---|---|---|---|
| | SPS (N = 488/44) | Placebo (N = 491/69) | | |
| Minimal | 13 (29.55) | 19 (27.54) | 0.289 | 0.6278 |
| Mild | 14 (31.82) | 17 (24.64) | 0.590 | |
| Moderate | 9 (20.45) | 17 (24.64) | 0.117 | |
| Severe | 1 (2.27) | 2 (2.90) | — | |
| Unknown | 7 (15.91) | 14 (20.28) | — | |
| Total | 44 (100.0) | 69 (100.0) | | |

As shown in Table 4, there was no obvious difference or shift in the spectrum of severity of post-ERCP pancreatitis between the two groups. While sPS treated patients had significantly fewer cases of pancreatitis, secretin did not seem to exert an obvious temporizing effect on the cases, which did occur relative to placebo. There were many cases of unknown severity, and it is possible there was a modest effect in terms of reducing severity, which was not visible because of the missing severity data.

The frequency of post-ERCP pancreatitis was evaluated in numerous patient sub-populations defined by the types of procedures performed during the ERCP. These results are described in Table 5.

TABLE 5

Incidence of Post-ERCP Pancreatitis in Patient Sub-Populations

| Procedure Related Sub-Populations | Treatment Group | | p-value |
|---|---|---|---|
| | SPS | Placebo | |
| Cannulation of CBD | N = 361 | N = 368 | |
| Yes (%) | 27 (7.48) | 56 (15.22) | 0.0010* |
| No (%) | 334 (92.52) | 312 (84.78) | |
| Cannulation of Pancreatic Duct | N = 220 | N = 219 | |
| Yes (%) | 30 (13.64) | 42 (19.18) | 0.1237 |
| No (%) | 190 (86.36) | 177 (80.82) | |

TABLE 5-continued

Incidence of Post-ERCP Pancreatitis in Patient Sub-Populations

| | Treatment Group | | |
|---|---|---|---|
| Procedure Related Sub-Populations | SPS | Placebo | p-value |
| Sphincterotomy of CBD | N = 140 | N = 159 | |
| Yes (%) | 7 (5.00) | 33 (20.75) | 0.0001* |
| No (%) | 133 (95.00) | 126 (79.25) | |
| Sphincterotomy of Pancreatic Duct | N = 26 | N = 30 | |
| Yes (%) | 12 (46.15) | 8 (14.29) | 0.1666 |
| No (%) | 14 (57.85) | 22 (73.33) | |
| Stent Removal from CBD | N = 58 | N = 59 | |
| Yes (%) | 1 (1.72) | 3 (5.08) | 0.6185 |
| No (%) | 57 (98.28) | 56 (94.92) | |
| Stent Removal from Pancreatic Duct | N = 17 | N = 17 | |
| Yes (%) | 2 (11.76) | 1 (5.88) | 1.0000 |
| No (%) | 15 (88.24) | 16 (94.12) | |
| Stent Insertion into CBD | N = 108 | N = 116 | |
| Yes (%) | 3 (2.78) | 10 (8.62) | 0.0856 |
| No (%) | 105 (97.22) | 106 (91.38) | |
| Stent Insertion into Pancreatic Duct | N = 23 | N = 42 | |
| Yes (%) | 5 (21.74) | 8 (19.05) | 1.0000 |
| No (%) | 18 (78.26) | 34 (80.95) | |
| Stone Extraction (Basket) | N = 35 | N = 48 | |
| Yes (%) | 1 (2.86) | 6 (12.50) | 0.2298 |
| No (%) | 34 (97.14) | 42 (87.50) | |
| Stone Extraction (Balloon) | N = 55 | N = 70 | |
| Yes (%) | 4 (7.27) | 6 (8.57) | 1.0000 |
| No (%) | 51 (92.73) | 64 (91.43) | |
| Manometry of CBD | N = 19 | N = 17 | |
| Yes (%) | 4 (21.05) | 9 (52.94) | 0.0819 |
| No (%) | 15 (78.95) | 8 (47.06) | |
| Manometry of Pancreatic Duct | N = 11 | N = 7 | |
| Yes (%) | 5 (45.45) | 5 (76.43) | 0.3665 |
| No (%) | 6 (54.58) | 2 (28.57) | |

*Fisher Exact Test

This analysis indicates that the intra-ERCP procedures most associated with the risk of developing post-ERCP pancreatitis are cannulation of the CBD, cannulation of the pancreatic duct and sphincterotomy of the CBD. There is the suggestion that sphincterotomy of the pancreatic duct, stent insertion into the pancreatic duct and manometry of both the CBD and pancreatic duct may also be associated with a higher increase of post-ERCP pancreatitis but the sample size was too small to be conclusive.

Further evaluation of the intra-ERCP procedures with meaningful sample sizes, which are associated with a higher risk of post-ERCP pancreatitis, i.e. cannulation of the CBD, and pancreatic duct, and sphincterotomy of the CBD demonstrates a highly significant protective effect of sPS. For cannulation of the CBD, the p-value=0.0010 and for sphincterotomy of the CBD, p<0.0001. For cannulation of the pancreatic duct, the p-value did not reach statistical significance (p=0.1237) but there was a numerical trend in favor of a preventive effect for sPS. Stent insertion into the CBD also showed a strong numerical trend in favor of sPS exerting a protective effect (3/108=2.78% for sPS vs. 10/116=8.62% for placebo) with the p-value of 0.0856 narrowly missing statistical significance. Manometry of the CBD almost demonstrates a statistically significant effect in favor of sPS (4/19=21.05%) vs. placebo (9/17=52.94%) with a p-value of 0.0819. The sample size, however, was small.

Additional secondary efficacy analyses were performed on post-ERCP pain, nausea, and vomiting using a 0 to 10 digital scale. There were no significant differences between the treatment groups for baseline (pre procedure) pain, nausea and vomiting. There were also no significant differences in these variables post-ERCP although there was a slight numerical trend indicating less nausea for sPS (p=0.0284).

Analysis of the differences between pre and post-ERCP pain, nausea and vomiting showed statistically significant increases for both treatment groups for each variable. The mean increases, however, were numerically smaller for the sPS group for each of the three variables and achieved statistical significance for nausea. These results are shown in Table 6.

TABLE 6

Pain, Nausea, Vomiting

| | Treatment Group | | |
|---|---|---|---|
| Parameter (Mean) | SPS | Placebo | p-value |
| Pain Pre-ERCP (SD) | 1.4 (0.6) (N = 483) | 1.4 (0.6) (N = 487) | 0.0668* |
| Pain Post-ERCP (SD) | 1.8 (3.0) (N = 485) | 2.2 (3.3) (N = 487) | |
| Change in Pain (SD) | 0.4 (3.4) (N = 480) | 0.8 (7.3) (N = 483) | |
| Nausea Pre-ERCP (SD) | 0.6 (1.7) (N = 483) | 0.6 (1.8) (N = 487) | 0.0284* |
| Nausea post-ERCP (SD) | 0.9 (2.1) (N = 485) | 1.3 (2.4) (N = 487) | |
| Change in Nausea (SD) | 0.3 (2.5) (N = 480) | 0.7 (2.6) (N = 483) | |
| Vomiting pre-ERCP (SD) | 0.1 (0.8) (N = 482) | 0.1 (0.5) (N = 486) | 0.0776* |
| Vomiting post-ERCP (SD) | 0.6 (1.9) (N = 485) | 0.8 (2.1) (N = 487) | |
| Change in Vomiting (SD) | 0.5 (2.0) (N = 479) | 0.7 (2.1) (N = 482) | |

*Fisher Exact Test

The symptoms and signs associated with pancreatitis (pain, nausea and vomiting), were identical in scored severity pre-ERCP but in each case showed much less of an increase post-ERCP in the sPS group. These between group differences in change reached significance for nausea and narrowly missed significance for pain and vomiting.

Additional secondary efficacy variables assessed were return to baseline (pre-ERCP levels of activity) and the time in days to return of pre-ERCP activity levels. There was a small difference in the percentage of patients reporting return to baseline activity within the follow-up period (2 to 4 days post-ERCP) favoring the placebo group (p=0.0230) (49.78% vs. 42.09%). Interims of the mean number of days required to achieve pre-ERCP activity levels, was 0.6 (±1.0) for the sPS group and 0.7 (±0.9) for the placebo group. An attempt was made to obtain information on return to work. Relatively few data points were able to be collected, however, because a large percentage of patients were not working pre-ERCP (retired, too ill, etc.) among the 185 patients (95 in the sPS group and 90 in the placebo group) providing relevant responses for this variable, 46.32% of sPS patients and 50.00% of placebo patients reported returning to work within the follow-up period. These results were not significant.

The results of this large, randomized, double-blind, placebo controlled study demonstrates a highly statistically significant protective effect for sPS in terms of preventing post-ERCP pancreatitis, i.e. decreasing the incidence relative to placebo. This finding applied to the overall study population and to several patient sub-populations defined by the intra-ERCP procedures performed. The effectiveness if sPS in decreasing the occurrence of post-ERCP pancreatitis was most evident in the sub-groups who underwent cannulation of the CBD and sphincterotomy of the CBD, but also seen in patients who underwent cannulation of the pancreatic duct, stent insertion into the CBD and management of the CBD.

7. Safety Evaluation

The adverse events (AE) observed in this study are summarized in Tables 7 and 8 below.

TABLE 7

Patients with Adverse Events

| Parameter (%) | Treatment Group | | |
|---|---|---|---|
| | SPS (N = 488) | Placebo (N = 491) | p-value |
| Patients with any AE | 20 (4.1) | 6 (1.2) | 0.0052* |
| Patients with mild/moderate AE | 17 (3.5) | 6 (1.2) | 0.0208* |
| Patients with severe AE | 1 (0.2) | 1 (0.2) | 0.4985 |
| Patients with AE related to study drug | 1 (0.2) | 0 (0) | 0.4985 |
| Patients with serious AE | 0 (0) | 0 (0) | — |
| Patients with unknown severity to AE | 1 (0.2) | 0 (0) | — |

*Chi-Square Test

TABLE 8

Incidence of Adverse Events

| Parameter (%) | Treatment Group | | |
|---|---|---|---|
| | SPS (N = 488) | Placebo (N = 491) | p-value |
| Total No. of Aes | 25 (5.1) | 6 (1.2) | 0.0006* |
| Total No. of mild/moderate Aes | 21 (4.3) | 6 (1.2) | 0.0039* |
| Total No. of severe Aes | 2 (0.4) | 1 (0.2) | — |
| Total No. of AEs related to study drug | 1 (0.2) | 0 (0) | — |
| Total No. of serious Aes | 0 (0) | 0 (0) | — |
| Total No. of unknown severity to AE | 1 (0.2) | 0 (0) | — |

*Chi-Square Test

The number and frequency of patients with adverse events and adverse events themselves were small in both treatment groups. Almost all were mild to moderate and only one was judged by the investigator to be related to study drug. This was a drop in blood pressure in patient #16, a 67 year-old male. This was a mild AE of an hour duration.

There were a larger number of AEs and patients with AEs in the sPS group. The differences reached statistical significance. Since almost all the AEs were related to the ERCP procedure or the patients' underlying medical condition and not to study drug, it is unclear why this imbalance occurred. There were no serious AEs and no patient was discontinued from the study because of an AE.

There were no deaths, serious AEs, or adverse dropouts during this study. There were also no routine clinical laboratory assessments conducted as part of this study. Secretin is a natural gastrointestinal peptide hormone with well-characterized pharmacological effects and is now an approved drug.

Systolic and Diastolic blood pressure and pulse were measured for all patients' pre and post-ERCP procedure. The results by treatment group are shown in Table 9.

TABLE 11

Vital Signs (Systolic and Diastolic BP*, Pulse)

| Parameter (Mean) | Treatment Group | | p-value |
|---|---|---|---|
| | SPS | Placebo | |
| Systolic BP pre-ERCP (SD) | 142.3 (24.9) (N = 397) | 143.0 (25.8) (N = 392) | 0.0007[+] |
| Systolic BP post-ERCP (SD) | 131.0 (23.9) (N = 381) | 137.1 (25.4) (N = 383) | |
| Change in Systolic BP (SD) | −11.4 (29.2) (N = 378) | −6.4 (25.1) (N = 376) | |
| Diastolic BP pre-ERCP (SD) | 74.6 (12.8) (N = 397) | 75.0 (13.2) (N = 393) | 0.1163 |
| Diastolic BP post-ERCP (SD) | 68.7 (13.4) (N = 381) | 70.9 (14.2) (N = 382) | |
| Change in Diastolic BP (SD) | −6.0 (15.3) (N = 378) | −4.3 (14.4) (N = 376) | |
| Pulse pre-ERCP (SD) | 81.0 (15.7) (N = 397) | 82.5 (15.3) (N = 392) | 0.1324 |
| Pulse post-ERCP (SD) | 91.0 (20.4) (N = 381) | 90.2 (19.1) (N = 383) | |
| Change in Pulse (SD) | 9.7 (17.7) (N = 378) | 7.8 (16.8) (N = 376) | |

*BP in mm/Hg
[+]Chi-Square Test

The mean vital signs for patients in this study remained within normal limits and were little changed in both treatment groups. The only significant difference between the groups was for systolic BP, which decreased from pre to post-ERCP procedure on both groups but slightly more in the sPS group. This may be a random outcome or may relate to the slight vasodilating effect of secretin and other GI peptide hormones in the VIP family. The change in mean systolic BP was not clinically significant for either group and is largely attributable to the conscious sedation medications administered routinely during ERCP procedures.

As shown in the tables above, synthetic porcine secretin was safe and well tolerated in this study population of patients undergoing ERCP. Most of the adverse events observed were mild and transient and were related to the ERCP procedure or underlying medical conditions. Vital signs were similar in both groups and typical of the values expected during ERCP.

8. Discussion and Overall Conclusions

Synthetic porcine secretin was safe and effective in this population of patients undergoing ERCP in terms of the primary efficacy variable of preventing (decreasing the incidence) of post-ERCP pancreatitis. The magnitude of the decrease in the frequency of post-ERCP pancreatitis was 36.2%, which was highly significant (p=0.0137). This efficacy result was obtained in a large sample of patients (979) enrolled over 3 years.

In addition, examination of all the largest sub-populations in terms of intra-ERCP procedures demonstrated a statistically significant prevention effect of a strong numerical trend for sPS. This indicates that regardless of the specific intra-ERCP procedure performed, which often is not known to the endoscopist until the ERCP is well advanced, sPS can be administered at the start to decrease the incidence of post-ERCP pancreatitis.

Synthetic porcine secretin was safe and well tolerated in this patient population. Most AEs were mild, transient and unrelated to study drug. Vital signs were generally normal and typical for patients undergoing ERCP.

Synthetic porcine secretin is safe and well tolerated in patients during ERCP and provides medically statistically significant protection from the development of post-ERCP pancreatitis.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A method for reducing the incidence of post endoscopic retrograde cholangiopancreatography pancreatitis, consisting of the step of administering to a patient deemed to be at risk of developing post endoscopic retrograde cholangiopancreatography pancreatitis prior to undergoing endoscopic retrograde cholangiopancreatography (ERCP), a therapeutically effective amount of a pharmaceutical composition comprising secretin and a pharmaceutically acceptable carrier, wherein the effective amount is effective for reducing the incidence of post endoscopic retrograde cholangiopancreatography pancreatitis and wherein said pharmaceutical composition is administered before any cannulation procedures.

2. The method of claim 1, wherein said secretin is the naturally occurring form of secretin.

3. The method of claim 1, wherein said secretin is a synthetic form of secretin.

4. The method of claim 3, wherein said synthetic form of secretin is synthetic porcine secretin.

5. The method of claim 1, wherein said secretin is a genetically recombined form of porcine, bovine or human secretin.

6. The method of claim 1, wherein said pharmaceutically acceptable carrier is selected from the group consisting of ion exchangers, alumina, aluminum stearate, lecithin, serum proteins, human serum albumin, buffers, phosphates, glycine, sorbic acid, potassium sorbate, partial glyceride mixtures of saturated vegetable fatty acids, water, salts, electrolytes, protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

7. The method of claim 1, wherein said pharmaceutical composition comprises from about 2 to about 50 micrograms of secretin.

8. The method of claim 7, wherein said pharmaceutical composition comprises from about 10 to about 36 micrograms of secretin.

9. The method of claim 8, wherein said pharmaceutical composition comprises from about 15 to about 20 micrograms of secretin.

10. The method of claim 1, wherein said patient is a human.

11. A method for reducing the incidence of post endoscopic retrograde cholangiopancreatography pancreatitis, consisting of the step of administering to a patient deemed to be at risk of developing post endoscopic retrograde cholangiopancreatography pancreatitis prior to undergoing endoscopic retrograde cholangiopancreatography (ERCP), a pharmaceutical composition comprising from about 2 to about 50 micrograms of secretin and a pharmaceutically acceptable carrier, wherein said pharmaceutical composition is effective for reducing the incidence of post endoscopic retrograde cholangiopancreatography pancreatitis and wherein said pharmaceutical composition is administered before any cannulation procedures.

12. The method of claim 11, wherein said secretin is the naturally occurring form of secretin.

13. The method of claim 11, wherein said secretin is a synthetic form of secretin.

14. The method of claim 13, wherein said synthetic form of secretin is synthetic porcine secretin.

15. The method of claim 11, wherein said secretin is a genetically recombined form of porcine, bovine or human secretin.

16. The method of claim 11, wherein said pharmaceutically acceptable carrier is selected from the group consisting of ion exchangers, alumina, aluminum stearate, lecithin, human serum albumin, phosphates, glycine, sorbic acid, potassium sorbate, partial glyceride mixtures of saturated vegetable fatty acids, water, salts, protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof.

17. The method of claim 11, wherein said pharmaceutical composition comprises from about 10 to about 36 micrograms of secretin.

18. The method of claim 17, wherein said pharmaceutical composition comprises from about 15 to about 20 micrograms of secretin.

19. The method of claim 11, wherein said patient is a human.

20. A method for reducing the incidence of post endoscopic retrograde cholangiopancreatography pancreatitis in a human patient, consisting of the step of administering to a human patient deemed to be at risk of developing post endoscopic retrograde cholangiopancreatography pancreatitis prior to undergoing endoscopic retrograde cholangiopancreatography (ERCP), a pharmaceutical composition comprising from about 2 to about 50 micrograms of synthetic secretin and a pharmaceutically acceptable carrier selected from the group consisting of ion exchangers, alumina, aluminum stearate, lecithin, human serum albumin, phosphates, glycine, sorbic acid, potassium sorbate, partial glyceride mixtures of saturated vegetable fatty acids, water, salts, protamine sulfate, disodium hydrogen phosphate, potassium hydrogen phosphate, sodium chloride (saline), zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat, and combinations thereof;

wherein said pharmaceutical composition is effective for reducing the incidence of post endoscopic retrograde cholangiopancreatography pancreatitis, and wherein said pharmaceutical composition is administered before any cannulation procedures.

21. The method of claim 20, wherein said synthetic secretin is a genetically recombined form of porcine, bovine or human secretin.

22. The method of claim 20, wherein said pharmaceutical composition comprises from about 10 to about 36 micrograms of secretin.

23. The method of claim 22, wherein said pharmaceutical composition comprises from about 15 to about 20 micrograms of secretin.

* * * * *